United States Patent [19]

Spector

[11] Patent Number: 4,889,284

[45] Date of Patent: Dec. 26, 1989

[54] RECHARGEABLE AIR FRESHENER

[76] Inventor: Donald Spector, 380 Mountain Rd., Union City, N.J. 07087

[21] Appl. No.: 291,862

[22] Filed: Dec. 29, 1988

Related U.S. Application Data

[63] Continuation-in-part of Ser. No. 148,009, Jan. 25, 1988, abandoned.

[51] Int. Cl.$^4$ ............................................... A61L 9/04
[52] U.S. Cl. ........................................ 239/34; 239/211
[58] Field of Search ...................... 239/34, 47, 55, 56, 239/211; 446/268, 369

[56] References Cited

U.S. PATENT DOCUMENTS

| 1,660,085 | 2/1928 | Nassau | 239/211 X |
| 1,767,911 | 6/1930 | Berko | 239/211 |
| 2,618,892 | 11/1952 | Locks | 239/211 |
| 3,679,133 | 7/1972 | Sekiguchi | 239/34 |
| 4,341,348 | 7/1982 | Dearling | 239/34 |
| 4,346,059 | 8/1982 | Spector | 239/34 X |
| 4,535,935 | 8/1985 | Spector | 239/34 |

FOREIGN PATENT DOCUMENTS 228393  2/1925  United Kingdom ................. 239/

Primary Examiner—Andres Kashnikow
Assistant Examiner—William Grant
Attorney, Agent, or Firm—Michael Ebert

[57] ABSTRACT

A rechargeable air freshener in a figurative form that includes a body and a head section, and an outer casing of permeable fabric material whose contours define all sections of the figure. The interior of the casing and all sections thereof are stuffed with a compressible core of absorbent material having good wicking properties, the core rendering the figure soft and squeezable. Occupying an internal cavity of the core which extends from the body to the head section thereof is a self-contained fragrance dispenser constituted by a cylindrical can filled with a liquid fragrance, a depressible stem projecting from one end of the can terminating in an actuator head provided with a spray nozzle. The can is so placed in the cavity that the actuator head lies just below the scalp region of the head section of the casing. When, therefore, the user presses the scalp region of the figure, this actuates the dispenser to spray a mist of liquid fragrance onto the core material within the head section, the fragrance being absorbed thereby and being wicked throughout the core. The aromatic vapor volatilized from the outer surface of the core passes through the permeable casing and is discharged into the atmosphere.

10 Claims, 1 Drawing Sheet

U.S. Patent  Dec. 26, 1989  4,889,284
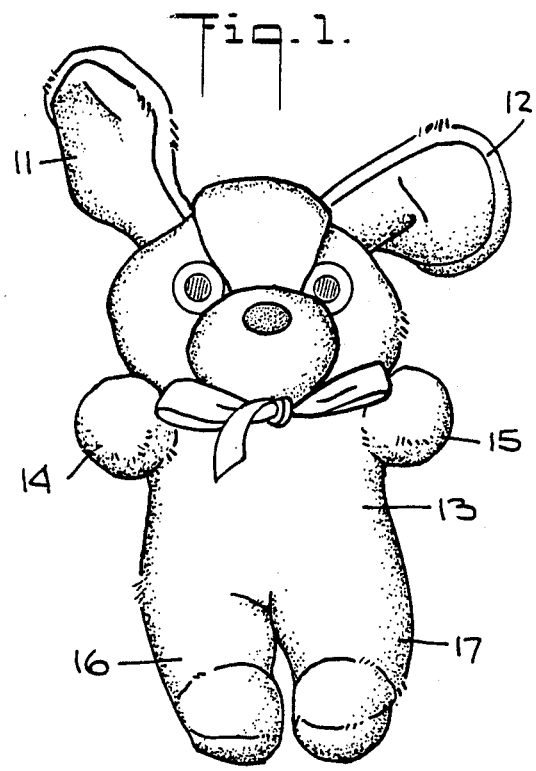
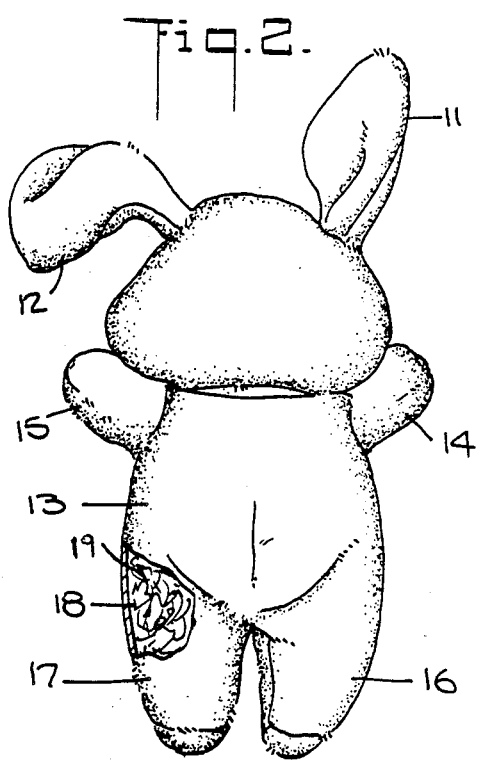
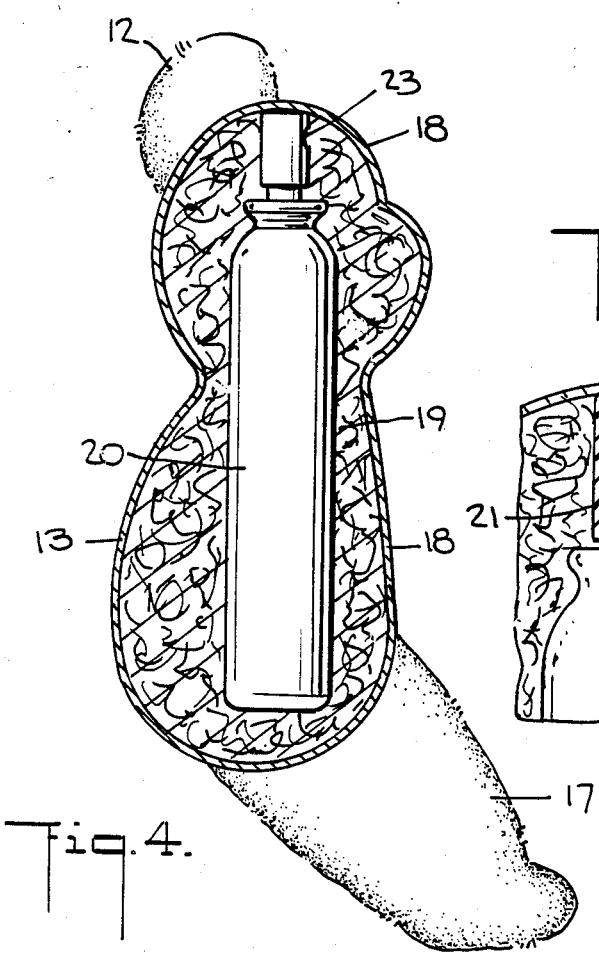
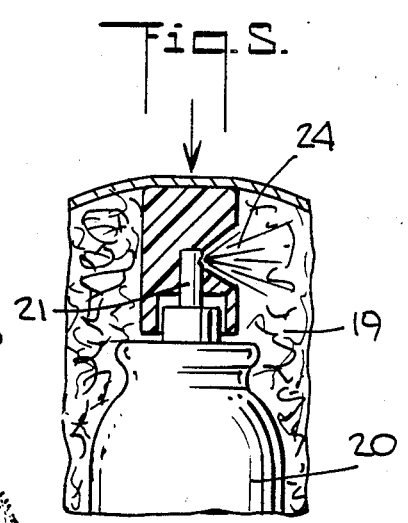
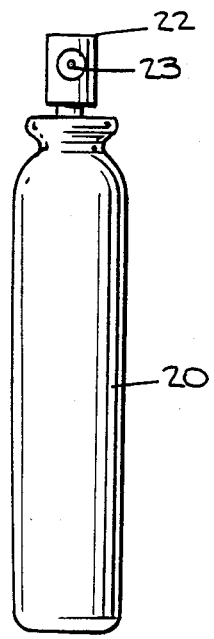

RECHARGEABLE AIR FRESHENER

RELATED APPLICATION

This application is a continuation-inpart of my copending application of the same title, Ser. No. 148,009, filed Jan, 25, 1988, now abandoned.

BACKGROUND OF INVENTION

1. Field of Invention

This invention relates generally to air fresheners which emit a pleasing fragrance into the atmosphere to mask unpleasant odors, and more particularly to a rechargeable air freshener in which an air-freshening scent is emitted in multiple directions from a decorative figure which also functions as a plaything.

2. Status of Prior Art

It is known to provide an air freshener in which a pleasing scent is emitted from a decorative figure. Thus my prior U.S. Pat. No. 4,535,935 discloses a rechargeable sachet in a snake-like format that may be coiled about a post or rod, the sachet including a permeable fabric sleeve stuffed with a flexible core of absorbent material having good wicking properties.

Within one end of the fabric sleeve is a socket which receives the corresponding end of the core, the base of the socket being provided with a projecting plug having an axial bore therein from which is extended a flexible dip tube. The plug is pressed into the mouth of a squeeze bottle containing liquid fragrance. By squeezing the bottle end of the sleeve, liquid fragrance from the squeezed bottle is injected into the end of the core and is wicked thereby throughout the body of the core. The liquid fragrance is volatilized from the surface of the core to produce an aromatic vapor which passes through the fabric sleeve and is discharged into the atmosphere. When the sachet core ceases to emit a scent, it is recharged by again squeezing the bottle end of the sleeve.

There are two practical drawbacks to my prior air freshener. The first is that the requirement for a cylindrical squeeze bottle as a liquid-fragrance reservoir which is inserted into one end of a cylindrical sleeve dictates a snake-like form and excludes other animal-like, fanciful or realistic figurative shapes.

The second practical drawback incident to the use of a squeeze bottle is that its operation is not accompanied by an audible sound that indicates whether the squeeze tube contains a liquid supply or is empty; for in both instances, when the bottle is squeezed, one hears virtually no sound. Hence the user of my prior sachet does not know when he has run out of liquid fragrance and he may continue futilely to squeeze the bottle.

It is also known to use as air fresheners, liquid fragrances contained under gas pressure in aerosol cans provided at one end with a projecting valve stem terminating in a nozzle head, such that when the head is actuated, an aromatic mist is sprayed from the nozzle head. The emission of the spray is accompanied by a hissing sound, and one knows that the fragrance is exhausted when the actuator head is pressed and no visible spray is then emitted and no hissing sound is heard.

In the typical air freshener of the aerosol type, one holds the can upright to spray the scent toward the center of the room so that its emission is unidirectional. Because of the strictly utilitarian appearance of an aerosol air freshener, it would be inappropriate to leave this air freshener on a desk or table of a well appointed room, such as a bedroom or living room. And because once the mist is unidirectionally discharged into a room, it is quickly dissipated, it is necessary to repeat the scent discharge action at fairly frequent intervals.

It is also known from the British patent to Hassler, 228,893, to provide a fragrance dispenser in the form of an animal-like figure which when squeezed emits a fragrance. This includes a liquid container and a squeeze bulb associated therewith which when actuated produces a spray that is emitted through the nose or eye opening of the figure. The figure itself does not emit a fragrance.

SUMMARY OF INVENTION

In view of the foregoing, the main object of this invention is to provide an air freshener in the form of a decorative animal-like or other fanciful or realistic play figure which disguises the function of the air freshener, making it feasible to place the freshener in rooms where an air freshener having a utilitarian appearance is socially acceptable.

A significant feature of the invention is that the design of the figure is not limited by freshener-dispenser requirements, and that it may assume any form, however, fanciful, as long as the figure includes a body section leading into a head section.

More specifically, an object of this invention is to provide an air freshener in a figurative format having an aerosol fragrance dispenser embedded therein such that the spray emitted by the dispenser is not visible, yet because the gas hiss which accompanies the spray ceases to be heard when the dispenser is exhausted, the user is advised when the fragrance dispenser is no longer operative. In another embodiment of the invention, the dispenser is of the pump type, such that when the head is pressed down, a metered amount of fragrance is emitted from the head.

Also an object of the invention is to provide a highly attractive air freshener which when exhausted continues to be a useful plaything or decorative toy.

Still another object of this invention is to provide an attractive air freshener which may be mass produced at low cost.

Briefly stated, these objects are attained in a rechargeable air freshener in a figurative form that includes a body and a head section, and an outer casing of permeable fabric material whose contours define all sections of the figure. The interior of the casing and all sections thereof are stuffed with a compressible core of absorbent material having good wicking properties, the core rendering the figure soft and squeezable.

Occupying an internal cavity in the core which extends from the body to the head section thereof is a fragrance dispenser constituted by a cylindrical can filled with liquid fragrance, a depressible stem projecting from one end of the can terminating in an actuator head provided with a spray nozzle. The can is so placed in the cavity that the actuator head lies just below the scalp region of the head section of the casing. When, therefore, the user presses the scalp region of the figure, this actuates the dispenser to spray a mist of liquid fragrance onto the core material within the head section, the fragrance being absorbed thereby and being wicked throughout the core. The aromatic vapor volatilized from the outer surface of the core passes through the permeable casing and is discharged into the atmosphere.

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a front view of a figure-like air freshener in accordance with the invention, one leg of the figure being cut away to expose the casing of the inner core:

FIG. 2 is a rear view of the air freshener;

FIG. 3 is an elevational view of the aerosol fragrance dispenser, shown separately;

FIG. 4 is a section taken through the figure shown in Fig. 1 to expose the core thereof and the aerosol dispenser embedded therein; and FIG. 5 is a detail showing the relationship between the scalp region in the head section of the figure casing and the actuator head of the aerosol fragrance dispenser.

DETAILED DESCRIPTION OF INVENTION

Referring now to FIGS. 1 and 2, there is shown an air freshener in accordance with the invention in the form of an animal-like figure having a head section 10 provided with upstanding ears 11 and 12, the head section being joined to a body section 13. Projecting outwardly from the body section 13 at the shoulders are a pair of short arm sections 14 and 15 (or front paws), while projecting downwardly from the body section 13 are a pair of leg sections 16 and 17 (or rear paws).

The invention does not reside in any particular form of figure which in practice may be in any realistic or fanciful form as long as it includes a head section of some sort joined to a body section. The figure is provided with an outer casing 18 that is shaped to define the contours of all sections of the figure. Casing 18 is fabricated of a permeable textile material such as velveteen, a fabric usually woven of cotton and made with a short, close pile in imitation of velvet, or it may be made of polyester plush with an even pile longer and less dense than velvet pile. The choice of fabric, which may be woven or non-woven or made of synthetic or natural fibers, depends on the nature of the figure, so that if the figure is, say, a polar bear with a heavy fur, a fabric having a thick pile is appropriate; whereas in other instances, the fabric may have no pile, such as satin or tricot.

All sections of the figure are stuffed with compressible core material 19 having good liquid absorbent and wicking properties, such as cotton batting or other soft, fibrous material. Or the core may be formed of highly absorbent paper-like fibers of the type used in modern baby diapers.

A preferred form of core is one whose outer layer which lies against the casing is of highly absorbent material, such as flexible foam plastic material, and an inner layer of material which has more pronounced wicking properties, such as cotton. In this way, the inner layer of the core which receives the fragrance from a dispenser buried in the core functions to transport the liquid fragrance by capillary action to the outer layer where the liquid is absorbed, from which outer layer the liquid is volatilized to produce an aromatic vapor that passes through the permeable fabric casing and is discharged in all directions into the atmosphere.

Because the core material which stuffs the fabric casing is compressible, the figure is soft and squeezable and therefore appealing and endearing to the user.

Formed in the central zone of core 19 is an internal cavity which runs the full length of the body section 13 into head section 13. The dimensions of the cavity are such as to snugly accommodate a self-contained air freshener dispenser in the form of a cylindrical aerosol can 20 containing a liquid fragrance under gaseous pressure, from whose upper end projects a depressible valve stem 21 terminating in an actuator head 22 provided with a lateral spray nozzle 23 that communicates with the hollow stem through which the liquid fragrance in the can is ejected.

The liquid fragrance contained in can 20 may be any natural or synthetic scent or a blend thereof, that includes fixatives which equalize vaporization and enhance pungency, these ingredients usually being combined with alcohol. The liquid fragrance may be of any known type in any desired concentration. Thus if the air freshener is intended for a child's nursery, the choice of scent will be different than an air freshener intended for a bathroom or bedroom.

The cavity within the core so orients the aerosol can that its actuator head 22 is placed just below the scalp region 10S of the head section 10, as best seen in FIGS. 4 and 5. Hence to operate the freshener, the user with his fingers simply presses down on scalp region 10S of the figure to depress actuator head 22 and thereby project from nozzle 23 a spray 24 of liquid fragrance which is directed toward the core material stuffed in head section 10.

Because of the wicking properties of the core, the liquid fragrance is transported by capillary action and by diffusion mechanisms throughout the core in all sections of the figure. As a consequence, the liquid scent is volatilized from the outer surface of the core in all sections of the figure to pass through the permeable casing to be discharged into the atmosphere. Hence the scent is emitted not from any limited section of the figure but in multiple directions from all sections thereof. Because the core retains the liquid fragrance and slowly discharges it into the atmosphere, one need actuate the aerosol can only at infrequent intervals.

In practice, the entire core may initially be saturated with liquid fragrance and the aerosol dispenser used as a reserve reservoir to recharge the core when the scent is exhausted. In that event, the figure must be stored in a hermetically sealed package to avoid shelf life loss of fragrance.

The only time it is necessary to operate the aerosol can actuator is when the scent emission from the figure ceases or is too low. Each time the aerosol can is actuated, because of the pressurized gas therein, even though one does see the spray, one hears the gaseous hiss. But when the can contents are exhausted, pressing the actuator head produces no hiss, thereby indicating that the can is now empty. In the embodiment shown, the aerosol can is sewn into the figure; hence it cannot be replaced. Alternatively, however, one can provide a figure with a Velcro closure at the crotch below the body section to permit the replacement of an exhausted can with a fresh can. But even with a figure in which the exhausted aerosol can cannot be replaced, the figure, though no longer an operative air freshener, remains useful as a play figure or toy.

Instead of using an aerosol can which contains a pressurized gas, the liquid fragrance may be contained in a cylindrical can provided with a pump type dispenser having an actuator head mounted on a hollow stem from which the liquid is sprayed out through a nozzle, the stem acting as the piston of the pump. This pump-type container may be buried in the core of the figure in the same manner as an aerosol can, with its actuator head just below the scalp region of the casing. The advantage of this pump-type dispenser is that each time the head is pressed down, a metered amount of liquid is dispensed regardless of how long the head is held down, whereas in an aerosol dispenser the amount of liquid dispensed depends on how long the head is held down.

This metered pump dispenser gives the user better control of the fragrance with respect to the fragrance requirements of the room in which the air freshener is placed. Thus the user can be instructed that for small rooms, the actuator head or button should be depressed three times; for medium size rooms five times, and for large rooms ten times. When, in time, the fragrance fades away, the air freshener is recharged by again operating the dispenser.

Also, the figure can serve as a plaything for a pet cat by filling the aerosol can with catnip. To excite the cat into play activity, the can is actuated to cause the figure to exude catnip. When the odor fades away, the cat will lose interest, which can be revived for the next play activity by again actuating the can.

While there has been shown and described a preferred embodiment of a rechargeable air freshener in accordance with the invention, it will be appreciated that many changes and modifications may be made therein without, however, departing from the essential spirit thereof.

I claim:
1. A rechargeable air freshener comprising:
    (a) an outer casing formed of permeable fabric material and contoured to define a figure including a head section and a body section joined thereto;
    (b) a core of compressible material stuffing all sections of the casing and having an internal cylindrical cavity therein, whereby the resultant figure is soft and squeezable, said material having liquid absorbent and wicking properties; and
    (c) a self-contained fragrance dispenser constituted by a cylindrical can whose diameter is substantially the same as the diameter of the cavity containing a volatile liquid fragrance, an axially-depressible head at the upper end of the can having a spray nozzle from which the liquid is sprayed when the head is depressed, said dispenser being disposed in said internal cavity which extends from the body section to the head section to place the actuator head at a position in the head section below a scalp region of the casing, whereby when pressing the scalp region to operate the actuator head, fragrance is sprayed into the core material in the head section and wicked thereby throughout the core material within the casing, the liquid fragrance volatilized from the outer surface of the core passing through the permeable casing to be discharged into the atmosphere.

2. An air freshener as set forth in claim 1, wherein said can is an aerosol can containing pressurized gas and includes a valve stem projecting from its upper end terminating in said head.

3. An air freshener as set forth in claim 1, wherein said can is provided with a pump having a hollow piston rod coupled to said head.

4. An air freshener as set forth in claim 1, wherein said casing is formed of cotton velveteen.

5. An air freshener as set forth in claim 1, wherein said casing is formed of polyester plush.

6. An air freshener as set forth in claim 1, wherein said casing is formed of satin.

7. An air freshener as set forth in claim 1, wherein said figure is animal-like and further includes arm and leg sections stuffed with said core material.

8. An air freshener as set forth in claim 1, wherein said core material is cotton batting.

9. An air freshener as set forth in claim 1, wherein said core material is diaper paper.

10. An air freshener as set forth in claim 1, wherein said core material is formed by an inner layer having good wicking properties and an outer layer having more pronounced absorbent properties.

* * * * *